United States Patent
Choi et al.

(10) Patent No.: US 10,932,999 B2
(45) Date of Patent: Mar. 2, 2021

(54) HYDROPHOBIC POROUS SILICA AND METHOD OF PREPARING HYDROPHOBIC POROUS SILICA

(71) Applicant: Research & Business Foundation Sungkyunkwan University, Suwon-si (KR)

(72) Inventors: Jae Young Choi, Suwon-si (KR); Su Dong Chae, Suwon-si (KR); Jang Ho Park, Suwon-si (KR); Sung Ho Lee, Seoul (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 16/553,331

(22) Filed: Aug. 28, 2019

(65) Prior Publication Data

US 2019/0380930 A1    Dec. 19, 2019

Related U.S. Application Data

(63) Continuation of application No. PCT/KR2017/008979, filed on Aug. 17, 2017.

(30) Foreign Application Priority Data

Mar. 31, 2017    (KR) .................. 10-2017-0041874

(51) Int. Cl.
*A61K 8/25*    (2006.01)
*A61K 8/02*    (2006.01)
(Continued)

(52) U.S. Cl.
CPC .............. *A61K 8/25* (2013.01); *A61K 8/0279* (2013.01); *A61K 8/31* (2013.01); *A61Q 19/10* (2013.01);
(Continued)

(58) Field of Classification Search
CPC .......... A61K 8/25; A61K 8/0279; A61K 8/31; A61K 2800/28; A61K 2800/622;
(Continued)

(56) References Cited

U.S. PATENT DOCUMENTS 2,736,669 A * 2/1956 Goebel ................ B01J 13/0069
427/220
2,801,185 A * 7/1957 Iler ........................ C01B 33/145
106/490
(Continued)

FOREIGN PATENT DOCUMENTS

JP    2008-105918 A    5/2008
JP    2011-088832 A    5/2011
(Continued)

OTHER PUBLICATIONS

Ballard et al., "Esterification of the Surface of Amorphous Silica," J. Phys. Chem. 1961, 65, 1, 20-25. (Year: 1961).*
(Continued)

*Primary Examiner* — Anthony J Zimmer
(74) *Attorney, Agent, or Firm* — NSIP Law

(57) ABSTRACT

A method of preparing hydrophobic porous silica includes adding an alcohol to a solvent in which a porous silica particle including a hydrophilic group is dispersed and stirring the same to form a mixture, drying the mixture including the porous silica particle in a vacuum, and condensation reacting the hydrophilic group of the porous silica particle with the alcohol on the surface of the porous silica particle to modify the surface of the porous silica particle to be hydrophobic.

5 Claims, 3 Drawing Sheets

CONDENSATION REACTION OF ALCOHOL MOLECULES WITH SILICA PARTICLES

CONDENSATION REACTION OF DIOL-BASED MOLECULES WITH SILICA PARTICLES

(51) Int. Cl.
*A61K 8/31* (2006.01)
*A61Q 19/10* (2006.01)
*C09C 1/30* (2006.01)

(52) U.S. Cl.
CPC ........ *C09C 1/3063* (2013.01); *A61K 2800/28* (2013.01); *A61K 2800/622* (2013.01)

(58) Field of Classification Search
CPC .. A61K 2800/612; A61K 8/585; A61Q 19/10; A61Q 19/00; C09C 1/3063; C01P 2006/19; C01B 33/18
See application file for complete search history.

(56) References Cited

U.S. PATENT DOCUMENTS

| | | | | |
|---|---|---|---|---|
| 5,928,723 A | * | 7/1999 | Koehlert | ............ C09C 3/08 427/213 |
| 6,579,929 B1 | * | 6/2003 | Cole | ............ C08K 9/04 524/492 |
| 2016/0326003 A1 | * | 11/2016 | Ishizuka | ............ C09C 1/30 |

FOREIGN PATENT DOCUMENTS

| | | |
|---|---|---|
| JP | 5394026 B2 | 1/2014 |
| KR | 10-2012-0105872 A | 9/2012 |
| KR | 10-1350843 B1 | 1/2014 |
| KR | 10-1416053 B1 | 7/2014 |
| WO | 2015/115184 A1 | 8/2015 |

OTHER PUBLICATIONS

International Search Report dated Dec. 18, 2017 in counterpart International Patent Application No. PCT/KR2017/008979 (2 pages in English and 2 pages in Korean).
Korean Office Action dated Oct. 19, 2017 in corresponding Korean Application No. 10-2017-0041874 (5 pages in Korean).

* cited by examiner

CONDENSATION REACTION OF ALCOHOL MOLECULES WITH SILICA PARTICLES

CONDENSATION REACTION OF DIOL-BASED MOLECULES WITH SILICA PARTICLES

| | AFTER COATING | AFTER 6 MONTHS OR MORE |
|---|---|---|
| DRY IN VACUUM |  |  |
| DRY IN NON-VACUUM |  |  |

HYDROPHOBIC POROUS SILICA AND METHOD OF PREPARING HYDROPHOBIC POROUS SILICA

CROSS-REFERENCE TO RELATED APPLICATIONS

This application is a continuation of International Application No. PCT/KR2017/008979 filed on Aug. 17, 2017, which claims the benefit of Korean Patent Application No. 10-2017-0041874 filed on Mar. 31, 2017, in the Korean Intellectual Property Office, the entire disclosures of which are incorporated herein by reference for all purposes.

BACKGROUND

1. Field

The present disclosure relates to a method of preparing a porous silica particle having a hydrophobically modified surface, to a hydrophobic porous silica particle thus prepared in which at least 90% of the surface area has been modified hydrophobically, and to a hydrophobic porous silica particle having 90% or more of the surface area being hydrophobic.

2. Description of the Background

In general, the skin consists of three layers of epidermis, dermis and subcutaneous fat tissue in order from the outside. It is a critical organization that not only protects the human body but also has biochemical and physical functions.

The skin is covered with sebum, sweat, dust, old dead skin cells, and the like, and thus, may cause acne and seborrheic dermatitis. Thus, cosmetics for removing sebum, sweat, dust, old dead skin cells, and the like are needed.

The cosmetics for removing dead skin cells are applied to the skin for use. The cosmetics may have a face-washing effect for effectively removing skin metabolism harmful substances, secretions, contaminants adhered from the outside, bacteria, make-up residue materials and the like; a massage effect for stimulating the nerves and blood vessels distributed in the dermis and subcutaneous tissues of the skin to function to promote blood flow, thereby preventing fine lines; and a peeling effect for preventing the thickening of the stratum corneum by making it possible to easily remove the keratinized keratin so as to keep the skin healthy and fresh.

Accordingly, studies have been conducted on the exfoliating cosmetics which do not cause skin damage and which can maintain moisture after exfoliation, and as a result, exfoliating cosmetics such as Korean Patent No. 10-1350843 or 10-1416053 have been developed.

Meanwhile, when particles used for the exfoliation cosmetics absorb moisture of the skin quickly, the user feels dry. Therefore, the porous particles used in the exfoliation cosmetics need to have hydrophobicity so that they can quickly absorb only the oil without absorbing the moisture.

However, the particles mainly used in conventional exfoliating cosmetics are made of plastic microbeads, and these microbeads have a problem that they are not decomposed because they have persistence. Therefore, the microbeads used for exfoliating cosmetics may be introduced into seawater, accumulated in marine organisms, and returned to humans through the food chain. Further, the microbeads may flow in the ocean and absorb various substances, resulting in a sharp increase in toxicity.

Therefore, porous silica particles have been in the spotlight as an alternative to microbeads. However, since the surfaces of general porous silica particles mainly consist of Si—OH bonds, they have hydrophilic properties.

In order for the porous silica particles to absorb the oil and have hydrophobicity at the same time, it is necessary to develop a technique of coating the surfaces of the outer wall of the pores uniformly and thinly to be hydrophobic without blocking the pores of the particles.

The above information is presented as background information only to assist with an understanding of the present disclosure. No determination has been made, and no assertion is made, as to whether any of the above might be applicable as prior art with regard to the disclosure.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In a first aspect of the present disclosure a method of preparing hydrophobic porous silica includes adding an alcohol to a solvent in which a porous silica particle including a hydrophilic group is dispersed and stirring the same to form a mixture, drying the mixture including the porous silica particle in a vacuum, and condensation reacting the hydrophilic group of the porous silica particle with the alcohol on the surface of the porous silica particle to modify the surface of the porous silica particle to be hydrophobic.

According to an embodiment of the present disclosure, the alcohol may include, but is not limited to, an alcohol represented by the following Chemical Formula 1:

　　　　　[Chemical Formula 1]

Here, $R_1$ may be a linear or branched alkyl group having C1 to C18 substituted or not substituted with an OH group, a linear or branched alkenyl group having C2 to C12, a cycloalkyl group having C3 to C12, or an aryl group having C6 to C12.

According to an embodiment of the present disclosure, the alcohol may include at least one —OH group, but is not limited thereto.

According to an embodiment of the present disclosure, the surface of the porous silica particle may be modified to be hydrophobic by the condensation reaction of the at least one —OH group contained in the alcohol with the hydrophilic group of the porous silica particle, but is not limited thereto.

According to an embodiment of the present disclosure, the solvent may be one selected from the group consisting of distilled water, ethanol, methanol, isopropyl alcohol, n-propyl alcohol, butanol, and combinations thereof, but is not limited thereto.

According to an embodiment of the present disclosure, the step of stirring the porous silica particle may be carried out at a speed of from 500 rpm to 4000 rpm, but is not limited thereto.

According to an embodiment of the present disclosure, the step of drying the porous silica particle in a vacuum may be carried out at a temperature from 70° C. to 150° C., but is not limited thereto.

According to an embodiment of the present disclosure, a hydrophobic porous silica particle may be prepared by the method, wherein at least 90% of the surface area of the porous silica particle is modified to be hydrophobic.

In a second aspect of the present disclosure, a hydrophobic porous silica particle includes a porous silica particle having a hydrophobic surface, wherein the hydrophobic surface includes 90% or more of the surface area of the porous silica particle.

The surface area may include surface area of inner pores of the porous silica particle.

The hydrophobic surface may include reaction product of diol molecules bonded to the porous silica particle surface.

The hydrophobic surface may include reaction product of alcohol molecules bonded to the porous silica particle surface.

The above-described technical solutions are merely exemplary and should not be construed as limiting the present disclosure. In addition to the exemplary embodiments described above, there may be additional embodiments in the drawings, the detailed description of the disclosure, and the claims.

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION

Figure 1:
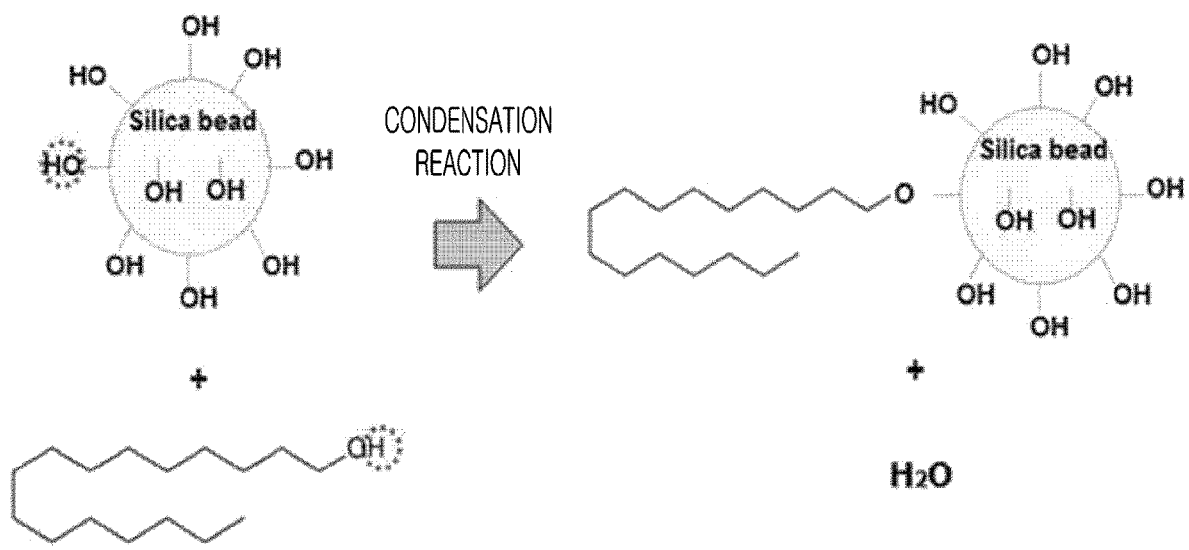
FIG. 1 is a schematic diagram showing that the surface of porous silica is polymerized with an OH group of alcohol, thereby modifying Si—OH of the surface to the hydrophobicity of Si—O—R, according to an embodiment of the present disclosure.
Figure 1:
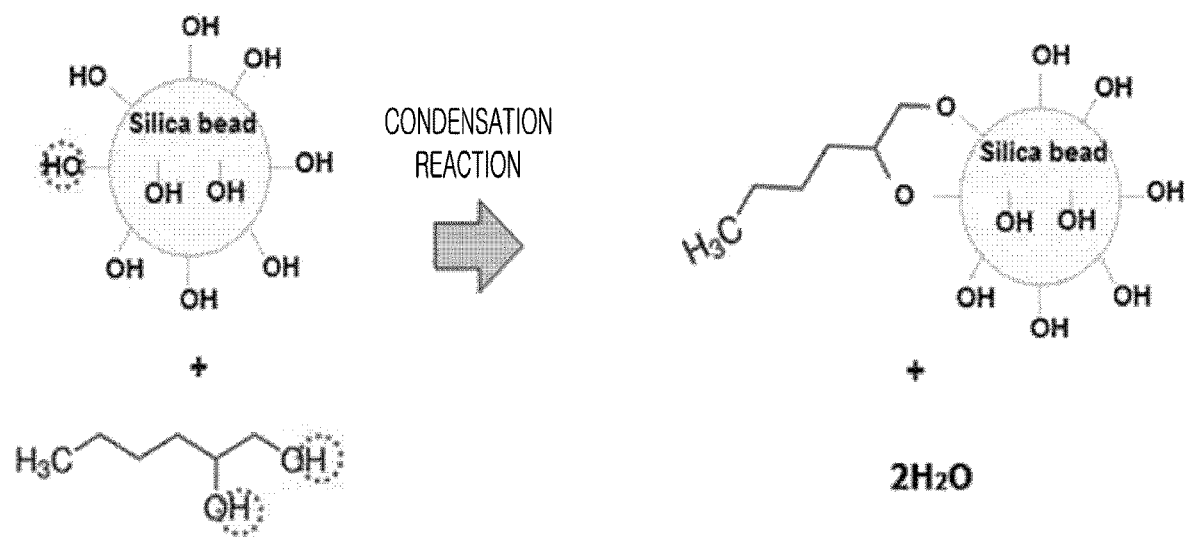

Hereinafter, the embodiments of the present disclosure will be described in detail with reference to accompanying drawings so that the embodiments may be easily implemented by those skilled in the art.

However, the present disclosure may be implemented in various ways without being limited to the embodiments. In addition, in the drawings, well-known elements or components may be omitted to avoid unnecessarily obscuring the presented embodiments, and like reference numerals denote like elements throughout the specification.

In the present disclosure, the term "connected to" or "coupled to" that is used to designate a connection or coupling of one element to another element includes both a case that an element is "directly connected or coupled to" another element and a case that an element is "electronically connected or coupled to" another element via still another element.

In the present disclosure, the term "on", "above", "upper", "under", "below", "bottom" that is used to designate a position of one element with respect to another element includes both a case that the one element is adjacent to another element and a case that any other element exists between these two elements.

In the present disclosure, when any portion "includes" any component, this does not exclude other components but means that any other component can be further included, unless stated otherwise.

In the present disclosure, the term representing the degree such as "about" and "substantially" means that any value is identical or close to a suggested numeral when an inherent fabrication error is proposed, and this is used for preventing any unscrupulous infringer from unfairly using the disclosure containing an exact or absolute numeral, which is mentioned for better understanding of the present disclosure. Further, in the entire specification of the present disclosure, a "step . . . " or a "step of . . . " does not mean a "step for . . . ."

In the present disclosure, the term "combination thereof" included in Markush-type expressions refers to a mixture or combination of one or more selected from the group consisting of components described by a Markush-type expression, and one or more selected from the group consisting of the components.

In the present disclosure, the description of "A and/or B" means "A, B, or A and B."

Herein, it is noted that use of the term "may" with respect to an example, for example, as to what an example may include or implement, means that at least one example exists in which such a feature is included or implemented while all examples are not limited thereto.

An object of the present disclosure is to provide a method for producing porous silica particles whose surface has been modified to be hydrophobic.

Another object of the present disclosure is to provide a hydrophobic porous silica particle prepared by the above-mentioned production method.

It should be understood, however, that the technical scope of the embodiments of the present disclosure is not limited to the above-described technical issues, but may include other technical issues.

According to the solution of the present disclosure as described above, the present disclosure may provide a method of preparing hydrophobic porous silica, which is capable of modifying the surface of the porous silica to have a hydrophobic property, and hydrophobic porous silica produced thereby.

In the manufacturing method of the present disclosure, the surface of the silica particles is modified from Si—OH to Si—O—R by polymerizing the OH group of the alcohol with the surface of the porous silica particles containing the hydrophilic group, thereby preparing a porous silica particle in which 90% or more of the surface is modified to be hydrophobic.

The hydrophobic porous silica according to the present disclosure has 90% or more of the porous surface having hydrophobicity, thereby increasing the water repellency and oil absorption so that the hydrophobic porous silica can be usefully applied to exfoliation cosmetics.

Hereinafter, a method of producing porous silica particles having a hydrophobically modified surface and hydrophobic porous silica particles produced by the method according to the present disclosure are described in detail with reference to embodiments, examples, and drawings. However, the present disclosure is not limited to these embodiments, examples and drawings.

The first aspect of the present disclosure relates to a method of preparing hydrophobic porous silica, in which the method includes adding an alcohol to a solvent in which a porous silica particle containing a hydrophilic group is dispersed and stirring the same to make a mixture, and drying the mixture including the porous silica particle in a vacuum, condensation reacting of the hydrophilic group of the porous silica particle with the alcohol on the surface of the porous silica particle to modify the surface of the porous silica particle to be hydrophobic.

The method of preparing hydrophobic porous silica according to the present disclosure allows polymerization of the surface of the porous silica particle containing a hydrophilic group with the OH group of the alcohol, thereby modifying the surface of the silica particles from a Si—OH to the Si—O—R (here, R represents a hydrophobic group contained in the alcohol). This makes it possible to produce hydrophobic porous silica in which 90% or more of the surface including pores is modified to be hydrophobic. The hydrophobic porous silica has improved water repellency and oil absorption, and thus can be usefully used in exfoliation cosmetics.

Particularly, the porous silica particle is dried in a vacuum so that 90% or more of the surface area including the pores of the porous silica particle can be uniformly coated with a hydrophobic molecule.

According to an embodiment of the present disclosure, the alcohol may, but is not limited to, including the alcohol represented by the following Chemical Formula 1:

R$_1$—OH                    [Chemical Formula 1]

Here, R$_1$ may be a linear or branched alkyl group having C1 to C18 substituted or not substituted with an OH group, a linear or branched alkenyl group having C2 to C12, a cycloalkyl group having C3 to C12, or an aryl group having C6 to C12.

The alkyl group, alkenyl group, cycloalkyl group or aryl group may all be substituted. The carbon number of the alkyl group, alkenyl group, cycloalkyl group or aryl group does not include the number of carbon atoms contained in the substituent group. Specific examples of the alkyl group and the substituent thereof may include a methyl group, an ethyl group, an n-propyl group, an isopropyl group, an n-butyl group, a t-butyl group, a n-hexyl group, a n-decyl group, a trifluoromethyl group, 3,3,3-trifluoropropyl group, 3-glycidoxypropyl group, 2-(3,4-epoxycyclohexyl) ethyl group, [(3-ethyl-3-oxetanyl) methoxy] propyl group, 3-aminopropyl group, 3-mercaptopropyl group, 3-isocyanate propyl group, and the like. Specific examples of the alkenyl group and substituent thereof may include a vinyl group and the like. Specific examples of the aryl group and substituent thereof may include a phenyl group, a tolyl group, a p-hydroxyphenyl group, a condensed polycyclic aromatic hydrocarbon group such as a naphthyl group, a phenanthrenyl group, a fluorenyl group, a pyrenyl group, an indenyl group, an acenaphthenyl group and the like.

According to an embodiment of the present disclosure, the alcohol represented by the above-described Chemical Formula 1 may include one or more —OH groups, but is not limited thereto.

The alcohol represented by the above-described Chemical Formula 1 may be selected from the group consisting of primary alcohol such as cetyl alcohol, lauryl alcohol, myristyl alcohol, lauryl-myristyl alcohol, lauryl-cetyl alcohol, caprylic alcohol, capric alcohol, stearyl alcohol, cetyl-stearyl alcohol and decyl alcohol and/or secondary alcohol such as hexanediol, propanediol, butanediol, pentanediol, and octanediol, but is not limited thereto.

According to an embodiment of the present disclosure, the surface of the porous silica particles may be modified to be hydrophobic by the condensation reaction of at least one —OH group contained in the alcohol with the hydrophilic group of the porous silica particles, but is not limited thereto.

Referring to FIG. 1 of the present disclosure, a method of modifying the surface of porous silica particle to be hydrophobic may be described, for example, using cetyl alcohol or 1,2-hexanediol as alcohol. When the porous silica particles containing a hydrophilic group and cetyl alcohol or 1,2-hexanediol containing at least one hydroxy group are reacted in a liquid phase condition, the hydrogen of the alcohol may be quickly condensed with the hydrophilic group on the surface of the porous silica particle so that $H_2O$ is generated and an alkoxy group is attached to the surface of the silica particle to coat the surface of the silica particle.

According to an embodiment of the present disclosure, for example, when cetyl alcohol or myristyl alcohol is used as the alcohol, each alcohol may be mixed with a C1 to C4 alcohol, and then the mixture may be sonicated to be used, but is not limited thereto.

According to an embodiment of the present disclosure, the solvent may be one selected from the group consisting of distilled water, ethanol, methanol, isopropyl alcohol, n-propyl alcohol, butanol, and combinations thereof, but is not limited thereto.

According to an embodiment of the present disclosure, the stirring step may be carried out at a speed of 500 rpm to 4000 rpm, but is not limited thereto.

When the stirring step is carried out at a speed of less than 500 rpm that is not within the above-mentioned range, the reaction may not be completed so that the surface of the porous silica particles may not be coated uniformly. When the stirring step is carried out at a speed of 4000 rpm or more, the alcohol may be evaporated.

According to an embodiment of the present disclosure, the step of drying the porous silica particle in a vacuum may be performed at a temperature of from 70° C. to 150° C., but is not limited thereto.

The porous silica particle is dried in a vacuum so that 90% or more of the surface area with the pores of the porous silica particles can be uniformly coated with hydrophobic molecules.

In the case of drying the particle in a vacuum as described above, since the pores of the particle are easily impregnated with a solvent, for example, a mixed solution of alcohol and water, the particles dried in vacuum may have an excellent uniform coating property of inner pores.

The second aspect of the present disclosure relates to a hydrophobic porous silica particle prepared by the above-described method, wherein at least 90% of the surface area of the porous silica particles is modified to be hydrophobic.

The second aspect of the present disclosure relates to a hydrophobic porous silica particle, wherein at least 90% of the surface area is modified to be hydrophobic according to the first aspect of the present disclosure. Further detailed description that overlaps with the first aspect of the present disclosure will be excluded. However, although the further description is excluded, the description of the first aspect of the present disclosure may be applied equally to the second aspect of the present disclosure.

Hereinafter, the present disclosure is described in more detail with reference to the following examples. However, the following examples are for illustrative purposes only and are not intended to limit the scope of the present disclosure.

Example 1. Modification of Surface of Porous Silica Particles Using Primary Alcohol In order to modify the surface of the porous silica particles to be hydrophobic, 20 g of cetyl alcohol was mixed with 20 g of ethanol, and then dissolved by sonication. 100 g of the porous silica particles was added thereto and the mixture was stirred at a speed of 3000 rpm for 20 minutes. After the stirring, the resultant was dried at 100° C. for one day by using a vacuum oven to obtain porous silica particles whose surface was modified to be hydrophobic. In another example to modify the surface of the porous silica particles to be hydrophobic, 20 g of myristyl alcohol was mixed with 20 g of ethanol, and then dissolved by sonication. 100 g of the porous silica particles was added thereto and the mixture was stirred at a speed of 3000 rpm for 20 minutes. After the stirring, the resultant was dried at 100° C. for one day by using a vacuum oven to obtain porous silica particles whose surface was modified to be hydrophobic.

Example 2. Modification of Surface of Porous Silica Particles Using Secondary Alcohol In order to modify the surface of the porous silica particles to be hydrophobic, first, 100 g of the porous silica particles was dispersed in 1 L of water. 40 g of 1,2-hexanediol was added to the solution in which the silica particles were dispersed, and the mixture was mixed using a mixer. Then, the solution containing the silica particles and 1,2-hexanediol was stirred at 1000 rpm for 30 minutes. After the stirring, the resultant was dried at 100° C. for one day by using a vacuum oven to obtain porous silica particles whose surface was modified to be hydrophobic.

Comparative Example. Porous Silica Particles without Drying in a Vacuum

In order to confirm the effect of vacuum drying in the preparation of the porous silica particles of the present disclosure, surface-modified porous silica particles were prepared in the same manner as in Example 1 above. In this regard, the resultant was dried in a non-vacuum condition to obtain porous silica particles.

Experiment Example 1. Evaluation of Hydrophobicity

The hydrophobic properties of the surface-modified hydrophobic porous silica particles by the alcohols prepared by the above Examples 1 and 2 were evaluated. As a comparative example, poly(methyl methacrylate) (PMMA) was used, which is a microbead commonly used for exfoliating cosmetics. It was purchased from SUNJIN BEAUTY SCIENCE in South Korea (PMMA1 (SUNPMMA-P20 Lot: 15106001) and PMMA2 (SUNPMMA-COCO130 Lot: 15120110)).

Specifically, 2 g of hydrophobic porous silica particles having surface-modified with primary alcohol or 2 g of hydrophobic porous silica particles having surface-modified with secondary alcohol were added to 100 ml of water, and the mixtures were stirred at 600 rpm for 30 seconds. 2 g of PMMA commonly used in exfoliating cosmetics was added to 100 ml of water, and the mixture was stirred at 600 rpm for 30 seconds. After 10 minutes, the transparencies of respective solutions were compared to confirm the hydrophobicities of respective particles.

Figure 2:
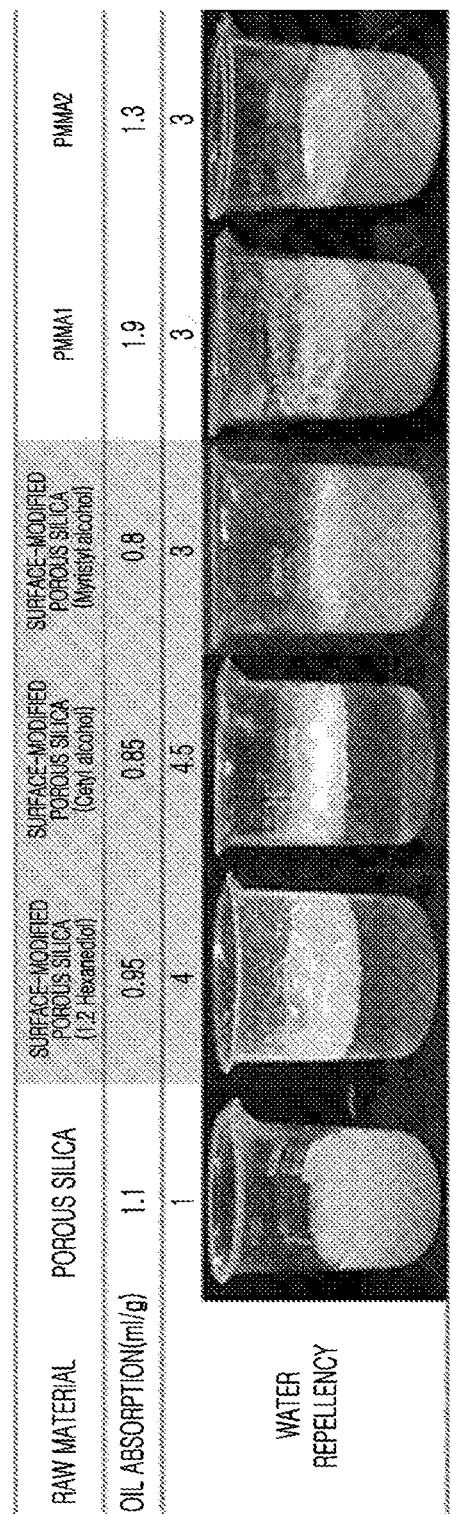
FIG. 2 shows the results of evaluating the hydrophobicity of the hydrophobic porous silica according to an embodiment of the present disclosure.

As shown in FIG. 2, the results indicate that the hydrophobic surface-modified porous silica particles of the present disclosure exhibited water repellency and oil absorption sufficient to replace PMMA. Meanwhile, the hydrophobic surface-modified porous silica particles showed a smaller oil absorption than the non-surface-modified porous silica particles. This is because not only the outer part of the porous silica particles but also the inner pores are coated with the hydrophobic molecules, and thus, the volume occupied by the pores is reduced. Therefore, it has been confirmed that the hydrophobic porous silica particles of the present disclosure can be applied to cosmetics that use conventional hydrophobic polymer beads.

Experiment Example 2. Comparative Evaluations of Water Repellencies by Vacuum/Non-Vacuum Drying The water repellencies of the hydrophobic porous silica particles dried in a vacuum prepared in Example 1 and the hydrophobic porous silica particles dried in a non-vacuum prepared in Comparative Example were compared and evaluated.

For this purpose, each 2 g of hydrophobic porous silica particles was added to 100 ml of water, and the degree of dispersion was confirmed after 6 months.

Figure 3:
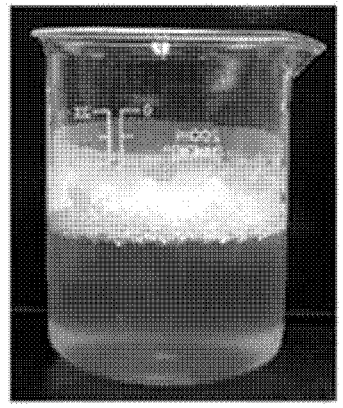
FIG. 3 shows the results of comparing the water repellencies of the hydrophobic porous silica upon vacuum/non-vacuum drying according to an embodiment of the present disclosure.
Figure 3:
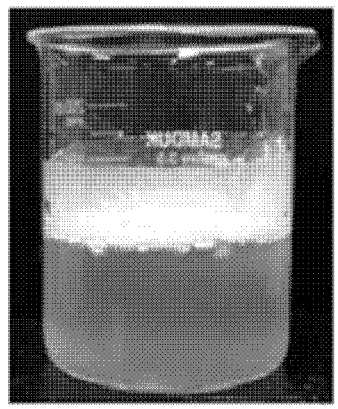
Figure 3:
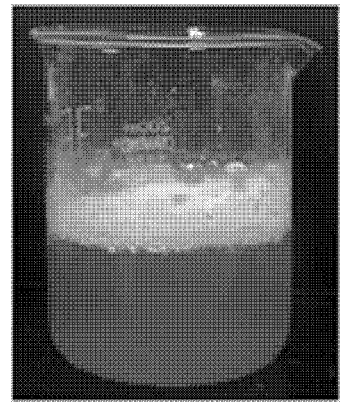
Figure 3:

As shown in FIG. 3, the results indicate that the hydrophobic porous silica particles dried in the vacuum of the present disclosure showed better water repellency than the hydrophobic porous silica particles dried in the non-vacuum even after 6 months.

Therefore, it was confirmed that the hydrophobic porous silica particles dried in the vacuum of the present disclosure had a large surface area coated with hydrophobicity, and the hydrophobic coating was applied to the inner pores, so that the water repellency was higher. On the other hand, it was confirmed that the hydrophobic porous silica particles dried in the non-vacuum had poor water repellency because the inner pores were not coated to be hydrophobic.

It will be understood by those of ordinary skill in the art that the foregoing description of the present disclosure is for illustrative purposes and that various specific embodiments may be easily implemented without departing from the technical spirit or essential characteristics of the present disclosure.

It is, therefore, to be understood that the above-described embodiments are illustrative in all aspects and not restrictive. For example, each component described as a singular form may be distributed and implemented, and components described as being distributed may also be implemented in a combined form. The scope of the present disclosure is defined by the appended claims rather than the detailed description, and all changes or modifications derived from the meaning and scope of the claims and their equivalents should be construed as being included within the scope of the present disclosure.

What is claimed is:

1. A method of preparing hydrophobic porous silica, comprising:
   adding alcohol to a solvent in which a porous silica particle comprising a hydrophilic group is dispersed and stirring the same to form a mixture;
   drying the mixture comprising the porous silica particle in a vacuum; and
   condensation reacting the hydrophilic group of the porous silica particle with the alcohol on the surface of the porous silica particle to modify the surface of the porous silica particle to be hydrophobic,
   wherein the alcohol is a primary alcohol selected from the group consisting of cetyl alcohol, myristyl alcohol, lauryl-myristyl alcohol, lauryl-cetyl alcohol, capric alcohol, cetyl-stearyl alcohol and decyl alcohol and/or a secondary alcohol selected from the group consisting of hexanediol, propanediol, butanediol, pentanediol, and octanediol, and wherein inner pores of the hydrophobic porous silica are hydrophobic to absorb an oil.

2. The method according to claim 1, wherein the surface of the porous silica particle is modified to be hydrophobic by the condensation reaction of at least one —OH group contained in the alcohol with the hydrophilic group of the porous silica particle.

3. The method according to claim 1, wherein the solvent is one selected from the group consisting of distilled water, ethanol, methanol, isopropyl alcohol, n-propyl alcohol, butanol, and combinations thereof.

4. The method according to claim 1, wherein the stirring step is carried out at a speed of from 500 rpm to 4000 rpm.

5. The method according to claim 1, wherein the step of drying the porous silica particle in a vacuum is carried out at 70° C. to 150° C.

* * * * *